United States Patent [19]

Lin

[11] Patent Number: 4,951,322

[45] Date of Patent: Aug. 28, 1990

[54] DETACHABLE MONO-GLASS SPORTS GOGGLES

[76] Inventor: David J. T. Lin, No. 2, Alley 24, Lane 9, Sec. 1 Nei Hu Road, Taipei, Taiwan

[21] Appl. No.: 413,036

[22] Filed: Sep. 27, 1989

[51] Int. Cl.$^5$ .................. A61F 9/02; G02C 5/02; G02C 5/12

[52] U.S. Cl. .................. 2/439; 2/441; 2/446; 2/454; 351/44; 351/132; 351/138

[58] Field of Search .................. 2/426, 439, 445, 446, 2/454, 441, 443; 351/41, 44, 88, 132, 138

[56] References Cited

U.S. PATENT DOCUMENTS

| | | | |
|---|---|---|---|
| 2,423,539 | 7/1947 | Williams | 351/44 |
| 2,582,345 | 1/1952 | Moeller | 351/44 |
| 3,233,249 | 2/1966 | Baratelli et al. | 351/44 |
| 3,233,250 | 2/1966 | Jonassen | 2/443 |
| 3,924,271 | 12/1975 | Hirschmann, Jr. | 2/439 |
| 4,867,550 | 9/1989 | Jannard | 351/47 |

FOREIGN PATENT DOCUMENTS

| | | | |
|---|---|---|---|
| 457706 | 6/1949 | Canada | 2/439 |
| 481478 | 3/1952 | Canada | 2/439 |
| 1105548 | 5/1954 | France | 2/439 |

Primary Examiner—Werner H. Schroeder
Assistant Examiner—Michael A. Neas
Attorney, Agent, or Firm—Varndell Legal Group

[57] ABSTRACT

A detachable mono-glass sports goggles includes a curved rod-like spectacle frame with two bows bilaterally connected thereto; an unitary glass having its top edge inserted into the bottom scoop channel of the spectacle frame; and a nose piece having an inverted V-shaped portion to support the unitary glass and to mount on user's nose, a split pin for insertion through the unitary glass into the spectacle frame to firmly retain the unitary glass therebetween, and a corrugated face portion for touching of fingers to correct the position of the goggles when it is in wear.

3 Claims, 3 Drawing Sheets

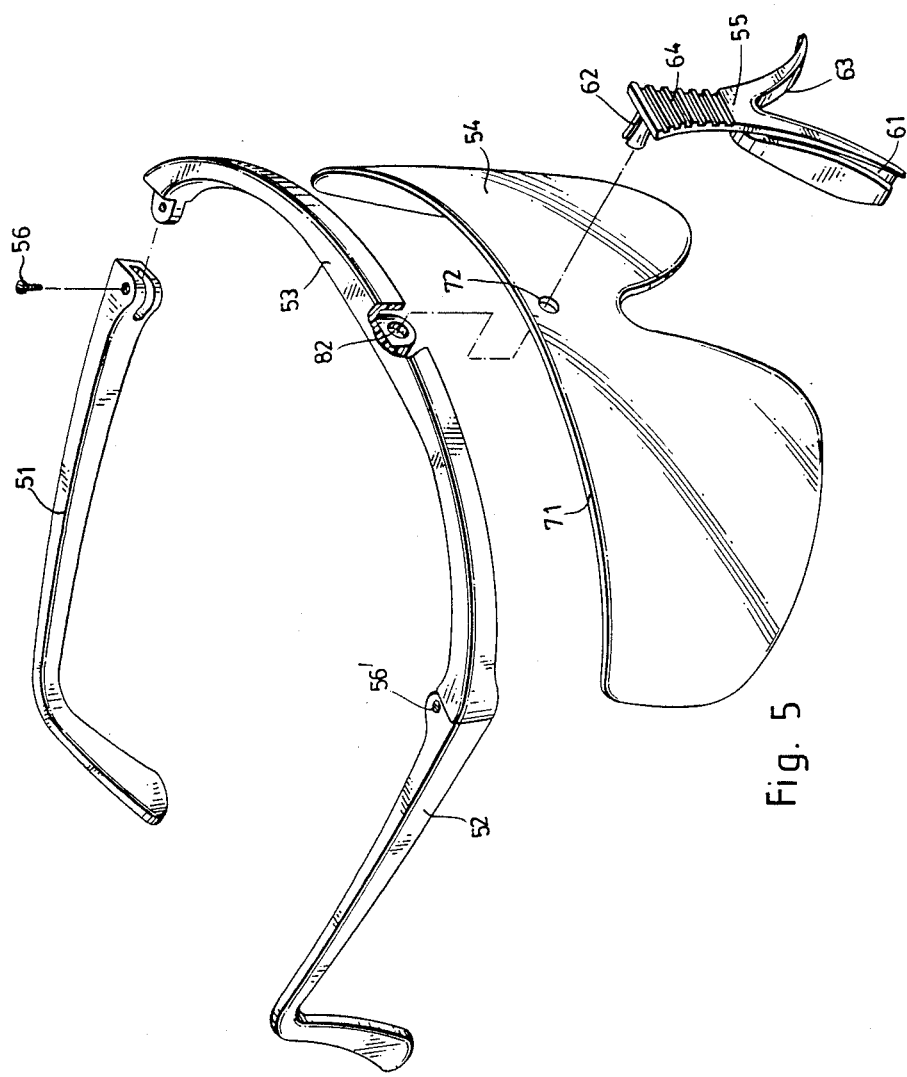

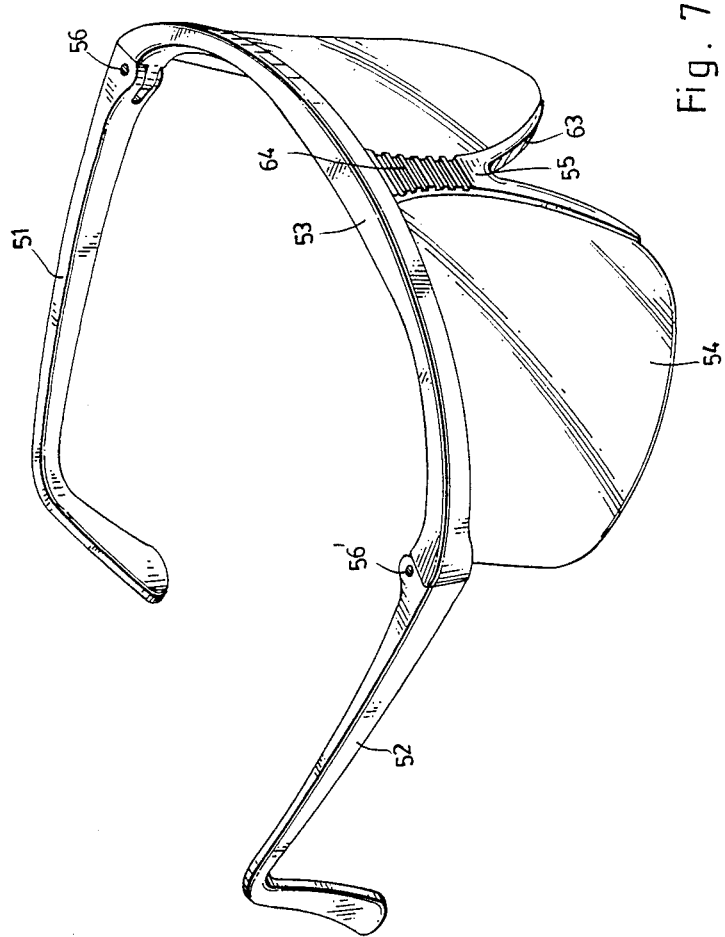

DETACHABLE MONO-GLASS SPORTS GOGGLES

BACKGROUND OF THE INVENTION

Sports goggles is a device commonly used during recreational and outdoor sports and activities to protect the eyes against dust, wind, sparks etc. In addition to functional requirement, light-weight, attractive outer appearance, high durability and safety are also important when one is considering to buy a sports goggle. However, according to conventional sports goggles, the said requirements are not possible to achieve at the same time.

Regular mono-glass sports goggles generally include two types, which are respectively outlined hereinafter:

FIGS. 1 and 2 illustrate a first type of conventional mono-glass sports goggles. In this type, the spectacle frame, bows, and unitary glass are made of plastic material through injection molding process. The two bows are respectively connected to the unitary glass by means of a fastening element made of metal material. The fastening element comprises two bolts for insertion into a pair of holes made in the unitary glass at both ends and a socket portion for insertion therein of the projecting lug of either one of the two bows. When the two bolts of a fastening element is inserted into either pair of holes of the unitary glass, the fastening element is firmly attached to the unitary glass by adhesive glue. The drawbacks of this type of sports goggles are as follows:

(1) Because stress is concentrated on the top edge of the unitary glass, the unitary glass tends to be deformed to cause the whole assembly of the goggles to slide when the goggles wearer is making an exercise;

(2) Because the unitary glass is connected with a bow by a metal fastening element, applied force and torque force in all directions may be concentrated on the unitary glass around the fastening elements to easily damage the unitary glass;

(3) Because the nose piece, either unitarily incorporated with the spectacle frame made through injection molding process or attached to the spectacle frame by adhesive joint, is disposed at the top of the unitary glass, the nose piece can not be smoothly and comfortably mounted on user's nose when in wear;

(4) The use of metal fastening elements makes the goggles relatively expensive;

(5) The unitary glass tends to be contaminated when one uses one's fingers to correct the position of the goggles;

(6) The component parts are not replaceable; and (7) The unitary glass is easy to deform due to the effect of outside force and temperature change when the goggles are received and not in use.

FIGS. 3 and 4 illustrate another type of conventional mono-glass sports goggles. In this type, the two bows, the spectacle frame and the unitary glass are made of plastic material through injection molding process. The unitary glass comprises two notches at both ends to define two female retaining members and is directly inserted into the bottom scoop channel of the spectacle frame with the two female retaining members respectively engaged with the bilateral male retaining members made internally on the spectacle frame. The drawbacks of this type of mono-glass sports goggles are outlines hereinafter:

(1) Because of the arrangement of male and female retaining members, the production of the sports goggles become more complicated and difficult. If the male and female members are not precisely made, the structure of a finished goggles will become unstable;

(2) Because the material strength between the spectacle frame and the unitary glass is different and the side edge of each female retaining member is very narrow, the connecting portion between the made and the female members may be easily damaged and the unitary glass may break away therefrom;

(3) The unitary glass is difficult to detach from the spectacle frame for cleaning and difficult to attach to the spectacle after cleaning;

(4) It is complicated to manufacture; and (5) The unitary glass tends to be contaminated when one uses one's fingers to correct the position of the goggles;

Further, in either of the said two types of conventional mono-glass sports goggles, the nose piece can not be smoothly and comfortably mounted on user's nose.

It is therefore, the main object of the present invention to provide such a detachable mono-glass sports goggles which is easy to assemble and detach.

Another object of the present invention is to provide such a detachable mono-glass sports goggles which utilizes a nose piece for smooth mounting on user's nose and for easy correction of the position of the goggles when the goggles are in wear.

A yet further object of the present invention is to provide such a detachable mono-glass sports goggles which includes a spectacle frame having a scoop channel made thereon for insertion therein of the top edge of a unitary glass, and a nose piece having a split pin made thereon for insertion through the unitary glass into the spectacle frame to let the unitary glass be firmly retained between the nose piece and the spectacle frame so as to let stress be uniformly distributed through the unitary glass.

The above and other objects and the advantages of the present invention will become apparent from the following detailed description of the preferred embodiment of the present invention referring to the annexed drawings in which:

BRIEF DESCRIPTION OF THE DRAWINGS

FIG. 5 is a perspective fragmentary view of a monoglass sports goggles embodying the present invention;

FIG. 6 is a sectional view of the nose piece according to the present invention; and FIG. 7 is a perspective assembly view of the present invention.

DETAILED DESCRIPTION OF THE PREFERRED EMBODIMENT

Figure 1:
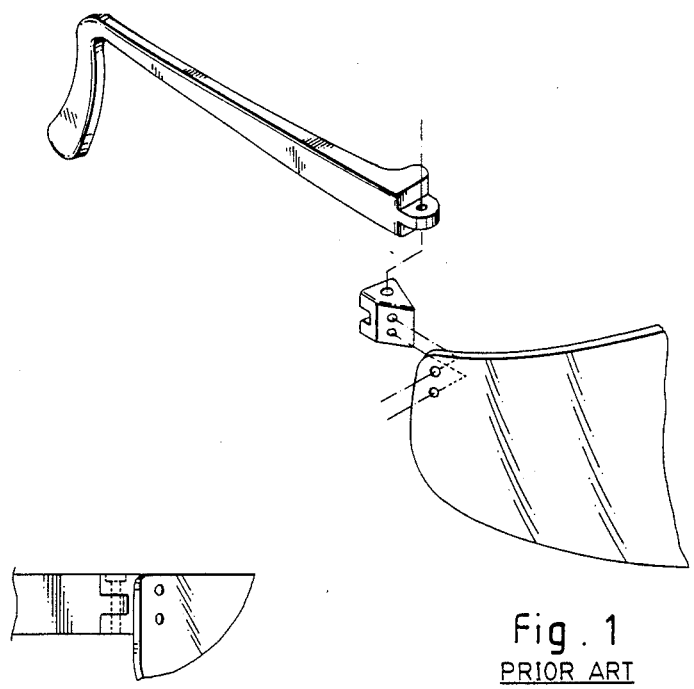
FIG. 1 is a partly structural fragmentary view of a conventional mono-glass sports goggles.
Figure 2:
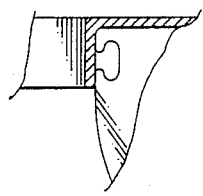
FIG. 2 is a partly structural assembly view of the sports goggles of FIG. 1 in which a bow is connected to a fastening element mounted on the glass.
Figure 3:
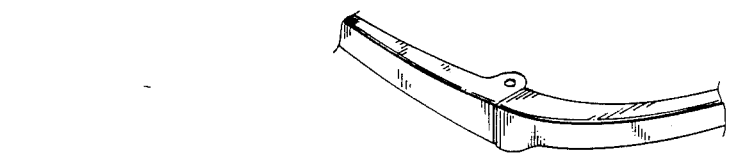
FIG. 3 is a partly structural fragmentary view of another type of conventional mono-glass sports goggles.
Figure 4:
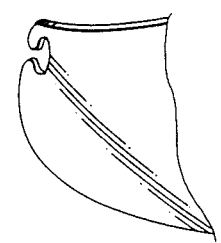
FIG. 4 is a sectional view of the mono-glass sports goggles of FIG. 3 in which a bow is connected to a mono-glass is connected to a spectacle frame.

Referring to FIGS. 5 through 7, therein illustrated is a mono-glass sports goggles embodying the present invention and generally comprised of a left bow (51), a right bow (52), a curved rod-like spectacle frame (53), a unitary glass (54), a nose piece (55), and screws (56) and (56').

The left bow (51) and the right bow (52) are respectively connected to the spectacle frame (53) at both ends by the screws (56) and (56') to respectively pivot thereto. The unitary glass (54) is mounted on the inverted V-shaped groove (61) of the nose piece (55) with its top edge (71) set in a scoop channel (81) made on the bottom edge of the spectacle frame (53), and at the same time, the split pin (62), which is made on the back side of the nose piece (55) at an upper position, is inserted through the hole (72), which is made on the unitary glass, into the hole (82), which is made on the spectacle frame (53) in the middle, to become firmly retained therein so as to let the unitary glass (54) be firmly attached to the spectacle frame (53). Thus, the spectacle frame (53) becomes the main structure to bear load. According to the present invention, the unitary glass (54) is properly arranged in a curvature to produce low stress and to let any stress be uniformly distributed. The nose piece (55) includes an inverted V-shaped portion (63) to smoothly attach to the nasal region of the user's nose, and a corrugated face portion (64) at the front for touching of fingers to drive the goggles to a comfortable position when they are in wear. Thus, it can be eliminated to contaminate the unitary glass (54) due to contact of hand when one corrects the position of the goggles on one's face.

Thus, as above described, a detachable mono-glass sports goggles of the present invention is easy to detach and assemble, of which the unitary glass is firmly retained against dropping or deformation, and the spectacle frame is more durable in use.

What is claimed is:

1. A detachable mono-glass sports goggles, including:
   a curved rod-like spectacle frame having a hole made thereon in the center;
   two bows respectively connected to said spectacle frame at both ends by means of screws;
   a unitary glass having a hole made thereon at a position opposite to the hole of said spectacle frame; and
   a nose piece comprising a split pin unitarily made thereon at the back side at an upper position for insertion through the hole of said unitary glass into the hole of said spectacle frame to allow said unitary glass to be firmly and detachably attached to said spectacle frame.

2. The detachable mono-glass sports goggles according to claim 1, wherein the nose piece includes an inverted V-shaped portion to smoothly attach to the nasal region of user's nose, said inverted V-shaped portion having an inverted V-shaped groove made thereon for mounting of said unitary glass, and a corrugated face portion for touching of fingers to correct the position of the goggles when it is in wear so as to prevent from contamination of said unitary glass.

3. The detachable mono-glass sports goggles according to claim 2, wherein said spectacle frame further comprises a scoop channel made on the bottom edge for insertion therein of the top edge of said unitary glass so as to let said unitary glass be firmly retained between said scoop channel of said spectacle frame and said inverted V-shaped groove of said nose piece when said split pin of said nose piece is inserted through the hole of said unitary glass into the hole of said spectacle frame.

* * * * *